(12) United States Patent
Giblin

(10) Patent No.: US 6,948,322 B1
(45) Date of Patent: Sep. 27, 2005

(54) SOLID STATE HEAT PUMP APPLIANCE WITH CARBON FOAM HEAT SINK

(76) Inventor: Percy Giblin, 9318 Pearsall Dr., Houston, TX (US) 77064

( * ) Notice: Subject to any disclaimer, the term of this patent is extended or adjusted under 35 U.S.C. 154(b) by 301 days.

(21) Appl. No.: 10/227,910

(22) Filed: Aug. 26, 2002

Related U.S. Application Data

(63) Continuation-in-part of application No. 09/950,304, filed on Sep. 10, 2001, now Pat. No. 6,438,964.

(51) Int. Cl.[7] ............................................. F25B 21/02
(52) U.S. Cl. ..................... 62/3.5; 62/3.62; 62/259.3
(58) Field of Search ................................ 62/3.5, 259.3, 62/3.6, 3.62

(56) References Cited

U.S. PATENT DOCUMENTS

| | | | | | |
|---|---|---|---|---|---|
| 4,470,263 | A | * | 9/1984 | Lehovee et al. .................. | 62/3 |
| 4,930,317 | A | * | 6/1990 | Klein ............................ | 62/3.3 |
| 5,197,294 | A | * | 3/1993 | Galvan et al. ................ | 62/3.62 |
| 5,970,718 | A | * | 10/1999 | Arnold ......................... | 62/3.5 |
| 6,023,932 | A | * | 2/2000 | Johnston ....................... | 62/3.5 |
| 6,033,506 | A | * | 3/2000 | Klett ............................ | 156/78 |
| 6,037,032 | A | * | 3/2000 | Klett et al. ................... | 428/71 |
| 6,125,636 | A | * | 10/2000 | Taylor et al. ................. | 62/3.5 |
| 6,257,011 | B1 | * | 7/2001 | Siman-Tov et al. ......... | 62/259.3 |
| 6,430,935 | B1 | * | 8/2002 | Klett et al. ................... | 62/3.3 |

* cited by examiner

*Primary Examiner*—Melvin Jones
(74) *Attorney, Agent, or Firm*—Kenneth A. Roddy

(57) ABSTRACT

A thermionic heating and cooling device for heating or cooling a portion of a user's body utilizes thermal diodes having a first surface in thermal contact with a flexible thermal transfer band strapped to a portion of the user's body and a second surface spaced apart therefrom with a thermally conductive porous carbon foam heat sink secured to their second surface which is partially enclosed by a shroud and a surrounding air filter. A small enclosure worn by the user contains an air pump, a battery and a switch. A flexible conduit connects the air pump and shroud and draws ambient air through the porous carbon foam medium. The thermal diodes are connected to the battery by leads extending through the conduit. A voltage bias between the diode surfaces creates a cold surface and hot surface opposite each other and causes electrons to flow in one direction and transfer heat from the first surface to the second and into the heat exchanger, and the heat is prevented from returning to the first surface.

21 Claims, 6 Drawing Sheets

SOLID STATE HEAT PUMP APPLIANCE WITH CARBON FOAM HEAT SINK

CROSS REFERENCE TO RELATED APPLICATION

This is a continuation-in-part of U.S. application Ser. No. 09/950,304 filed Sep. 10, 2001, now U.S. Pat. No. 6,438,964, and priority thereof is claimed.

BACKGROUND OF THE INVENTION

1. Field of the Invention

This invention relates generally to solid-state thermionic heating and cooling devices for thermally treating the human body, and more particularly to such a device that has a solidstate thermionic thermal diode unit with a carbon foam heat sink that provides greater surface area per unit volume and significantly greater heat transfer efficiency than conventional thermoelectric Peltier devices with finned heat sinks and facilitates miniaturization.

2. Description of the Related Art

Peltier effect thermoelectric heat pumping devices that are used for thermally treating (cooling or heating) the human body are known in the art. Such solid-state heat pumping devices typically contain a Peltier module, a heat sink and a fan. Most prior art Peltier devices utilize a heat sink that is comprised of a block of aluminum or copper having protruding fins from which heat is removed by radiation, natural convection or the forced convection of a fan. These types of prior art heat sinks are bulky and heavy and generally constitute the largest component of the heat pump device and thereby render the devices unsatisfactory for applications having size or weight restrictions. A fan placed in close proximity of the heat sink also adds to the size of the device.

Klein, U.S. Pat. No. 4,930,317 discloses a hot/cold therapy device having a hot/cold pad assembly remotely connected to a control module. The hot/cold pad assembly includes a flexible pad filled with a convection (gel) or conduction (laminated metal, rubber impregnated with metal particles, etc.), or combination thereof (a conductive metal layer immersed in a gel). A thin plate of conductive material (copper) forms an extension of the cold plate of a thermoelectric heat pump, both of which are in thermal contact with the pad. A finned air-cooled heat sink is mounted in a housing or shroud which is connected by a flexible umbilical line to the control module. The control module includes a fan for drawing or blowing air through the shroud to maintain the temperature difference between the finned heat sink and attached plate of the thermoelectric heat pump element.

Galvan et al, U.S. Pat. No. 5,197,294 discloses a miniaturized thermoelectric Peltier apparatus for air conditioning a protective body suit. The Peltier device, in the form of bimetallic or plurimetallic plates is connected to a low voltage D.C. power supply, the opposed cold and hot surface of which are in contact with respective finned heat exchangers. The assembly is contained in a housing in which two distinct and separate conduits are provided for the forced flow of air through the respective ones of the finned heat exchangers.

Arnold, U.S. Pat. No. 5,970,718 discloses a personal heat control apparatus having an outer casing that accommodates a Peltier-effect unit, one or more batteries and a timing switch for selective energization of the unit. The casing is releasably attached to a part of a person's body, e.g. the wrist, by a strap with a cooling surface cooled by the unit in contact with the body part to enhance heat transfer between the person's body and the surrounding air for comfort and refreshment purposes when the unit is energized. Heat generated in the unit is dispersed through the outer casing, which serves as the heat sink. The surface area of the heat sink (casing) may be several times the size of the cooling surface, e.g. five times larger, to promote rapid heat dissipation.

Johnston, U.S. Pat. No. 6,023,932 discloses a portable topical heat transfer device for topically cooling an animal or human which comprises a thermoelectric unit having a cold side and a warm side, a DC source which is connected to the thermoelectric unit, a finned heat sink which is mounted in a heat conductive relationship with the warm side of the thermoelectric unit, a fan for removing heat from the heat sink, and a strap or the like for securing the device to the body of the wearer. The heat sink comprises the main body portion of the device and includes a series of fins and channels.

Taylor et al, U.S. Pat. No. 6,125,636 discloses a self-contained personal cooling and/or heating device that includes a heat-dissipating member which fits around a portion of a user's body. A Peltier thermo-voltaic module operated with low voltage at relatively low current is thermally coupled to the rear surface of the member, and the rear surface of the module is provided with a large surface area, preferably augmented by a finned heat sink. A fan directs ambient air onto this rear module surface or heat sink.

Most of these prior art devices are unsatisfactory for personal cooling applications having size or weight restrictions because they utilize less efficient thermoelectric Peltier modules with one or more finned heat sinks formed of aluminum or copper which are bulky and heavy and generally constitute the largest component of the device, or they utilize a casing or housing of relatively large surface area that serves to dissipate heat. Some of these devices also utilize a fan in close proximity to the heat sink, which also adds to the size of the device. Recently developed "thermionic" temperature modification devices, also known as "vacuum diode heat pumps" or "thermal diodes", are solid-state semiconductor devices capable of alternating between heating and cooling of a particular element. Thermionic devices are similar in concept to thermoelectric (Peltier) devices, except that the thermal diode operates in the manner of a vacuum diode wherein the electrons move across a gap, which is an excellent insulator. The gap may also be evacuated to create a vacuum. With the addition of a voltage bias that encourages the electrons to move in a given direction, the heat is transferred from one side (cathode or emitter) to the other (anode or collector) across the gap between the two materials, and the gap prevents the heat from flowing back.

Tunneling diodes or resonant tunneling diodes (RTD) are small semiconductor chips that utilize ultra-thin layers wherein a "well" of silicon or other material is sandwiched between two barrier layers (for example silicon dioxide) with electrical contacts on the top and bottom, wherein, upon application of a voltage bias, electrons "tunnel" from one side of the barrier to the other. This movement is known as "tunneling". Resonant tunneling diodes (RTD) have also been made by growing extremely thin layers of chemically different semiconductors (such as gallium arsenide, GaAs, and aluminum arsenide, AlAs) on top of one another in a single crystal structure, wherein the layer of GaAs between layers of AlAs may be a few nanometers thick to form a well of finite depth for electrons.

Cool Chips plc., a subsidiary of Borealis Exploration Limited (BOREF), based in Gibralter, has recently developed a form of vacuum diode known as Cool Cool Chips™ that pump heat from one side of the chip to the other to provide localized cooling and refrigeration utilizing a "thermotunnel" technology based on known principles of quantum physics wherein electrons are made to "tunnel" from one side of a tiny vacuum gap (50 nanometers or less) to another. These devices are reported to deliver up to a projected 70–80% of the maximum theoretical efficiency for a perfect heat pump (known as Carnot Efficiency). The Borealis Cool Cool Chips™ and "thermotunnel" technology are disclosed in U.S. Pat. No. 6,417,060 and U.S. Pat. No. 6,285,769, which are hereby incorporated by reference to the same extent as if fully set forth herein.

Thermoelectric (Peltier) devices, on the other hand, do not have a gap and the electrons that carry heat in one direction flow through the material itself and most of that heat is returned through conduction. Conventional thermoelectric (Peltier) devices may achieve an efficiency of up to 5–8% of the theoretical maximum for a perfect heat pump (Carnot Efficiency). Thus, thermionic vacuum diode heat pump and thermal diode devices offer much higher efficiency, higher output cooling in a much smaller package, and require less power to operate, than is possible with thermoelectric (Peltier) devices.

U.S. Pat. No. 5,722,242 and U.S. Pat. No. 6,396,191, hereby incorporated by reference to the same extent as if fully set forth herein, teach the construction and operation of a vacuum diode heat pump, and a thermal diode, respectively. U.S. Pat. No. 6,417,060, hereby incorporated by,reference, discloses methods for making diode devices and electrodes that may be used in a diode device such as thermionic converters and generators, photoelectric converters and generators, vacuum diode heat pumps, and thermotunnel converters.

Although not a personal cooling device for thermally treating the human body, Klett et al, U.S. Pat. No. 6,430,935 discloses an air cooling filtering device for providing cool or warm filtered air for a person to breathe that includes at least one thermoelectric and/or thermionic element and at least one thermally conductive carbon foam element (described in detail hereinafter), which has at least one flow channel through which fluids (air) passes. The thermoelectric and/or thermionic device is thermally connected to the carbon foam element and modifies the temperature of the carbon foam, which in turn, modifies the temperature of air flowing through the flow channels. In a preferred embodiment, the thermoelectric and/or thermionic device is sandwiched between two carbon foam elements. This device does not place the cold or hot surface of the thermoelectric and/or thermionic member in thermal contact with the object to be cooled or heated, but instead teaches placing the foam material in thermal contact with the object to be cooled or heated (air). The thermoelectric and/or thermionic device merely serves to modify the temperature of the foam, and the object to be cooled or heated (air) passes from an inlet end to an outlet end of the flow channels in the foam, rather than being drawn through the cellular structure of the foam medium.

The carbon foam heat sink material utilized in U.S. Pat. No. 6,430,935 and also preferably in the present invention is a recently developed new material is produced by a patented foaming process disclosed in U.S. Pat. Nos. 6,033,506 and 6,037,032 issued to James W. Klett et al., and which are hereby incorporated by reference to the same extent as if fully set forth herein. This carbon foam material is commercially known as "PocoFoam"® marketed by Poco Graphite, Inc., of 1601 South Street, Decatur, Tex. 76234.

This new material is high thermal conductivity porous foam which allows the transfer of a large volume of thermal energy. The carbon or graphite aligned ligament structure conducts heat better than copper or aluminum. Its porous structure gives it an enormous surface area, such as two square meters per cubic centimeter of material. That is to say, a sugar cube sized piece of this material would have the surface area of forty-two square feet and weigh half a gram. Air is passed through its interconnecting porous network wherein heat is removed. In comparison, a sugar cube sized aluminum heat sink may have a surface area of a few square inches and may only transfer a minute amount of heat.

The present invention overcomes the size and weight limitations of the prior art and is distinguished over the prior art in general, and these patents in particular, by a miniaturized solid-state thermionic heating and cooling device for thermally treating the human body that utilizes thermionic thermal diodes which provides high efficiency, high output cooling in a very small package, and a carbon foam heat sink of porous open cell structure which provides greater surface area per unit volume and significantly greater heat transfer efficiency than conventional finned heat sinks. Miniaturization is further facilitated by placing the air pump and power supply unit remote from the thermionic heating and cooling unit to extract and dispose of heat collected from the carbon foam heat sink.

SUMMARY OF THE INVENTION

It is therefore an object of the present invention to provide a miniaturized solid-state thermionic heat pump for thermally treating the human body, which is sufficiently small to be worn and concealed beneath practically any type of hardhat, helmet, hazardous material suit, industrial or occupational wear, costumes, sporting or casual wear.

It is another object of this invention to provide a miniaturized solid-state thermionic heat pump for thermally treating the human body that utilizes thermionic thermal diodes or vacuum diode heat pumps, or tunneling diodes which conserve power, offer much higher efficiency, higher output cooling in a much smaller package, and require less power to operate, than is possible with thermoelectric Peltier devices.

Another object of this invention is to provide a miniaturized solid-state thermionic heat pump for thermally treating the human body that utilizes a carbon foam heat sink which is significantly smaller and lighter in weight than conventional finned heat sinks.

Another object of this invention is to provide a miniaturized solid-state thermionic heat pump for thermally treating the human body that utilizes a carbon foam heat sink of porous open cell structure to provide greater surface area per unit volume and significantly greater heat transfer efficiency than conventional finned heat sinks.

A further object of this invention is to provide a miniaturized solid-state thermionic heat pump for thermally treating the human body that utilizes a carbon foam heat sink of porous open cell structure and a remote heat extraction and discharge unit that extracts and discharges collected heat from the heat sink.

A still further object of this invention is to provide a miniaturized solid-state thermionic heat pump for thermally treating the human body that utilizes thermionic thermal diodes, vacuum diode heat pumps, or tunneling diodes, in combination with carbon foam heat sinks that is simple in construction, inexpensive to manufacture, extremely efficient, and rugged and reliable in operation.

Other objects of the invention will become apparent from time to time throughout the specification and claims as hereinafter related.

The above noted objects and other objects of the invention are accomplished by a miniature thermionic personal heating and cooling device for heating or cooling a portion of a user's body that utilizes a porous carbon foam heat sink secured to one surface of a thermionic thermal diode module. The heat sink is formed of a thermally conductive open cell foam medium through which air can pass and is partially enclosed by a shroud and a surrounding air filter. The opposed surface of the thermionic member is secured to a flexible thermal transfer band that is releasably strapped to a portion of the user's body. A miniature air pump and a battery are contained in a small enclosure that is releasably secured on another portion of the user's body remote from the thermal transfer band. A flexible tubular conduit connects the air pump inlet to the shroud and draws ambient air through the thermally conductive open cell foam medium. Electrical leads connected between the battery and the thermal diode modules extend through the flexible tubular conduit. An on/off switch on the enclosure selectively energizes the air pump and the thermal diodes. A polarity reversing switch on the enclosure supplies selected polarized electrical energy to the thermal diodes for cooling or heating. In a preferred embodiment, the open cell foam medium is a lightweight, porous graphite foam with an average pore diameter of approximately 350 microns (approximately 0.0138 inches) and has an effective heat exchanging surface area greater than about 4 $m^2/g$ (about 19500 $ft^2/lb$). Thus, the present invention provides significantly greater heat transfer efficiency and requires less power to operate than devices utilizing conventional thermoelectric Peltier devices with finned heat sinks. Miniaturization is further facilitated by placing the air pump and power supply unit remote from the thermionic heating and cooling unit to extract and dispose of heat collected from the carbon foam heat sink.

DESCRIPTION OF THE PREFERRED EMBODIMENT

Figure 1:
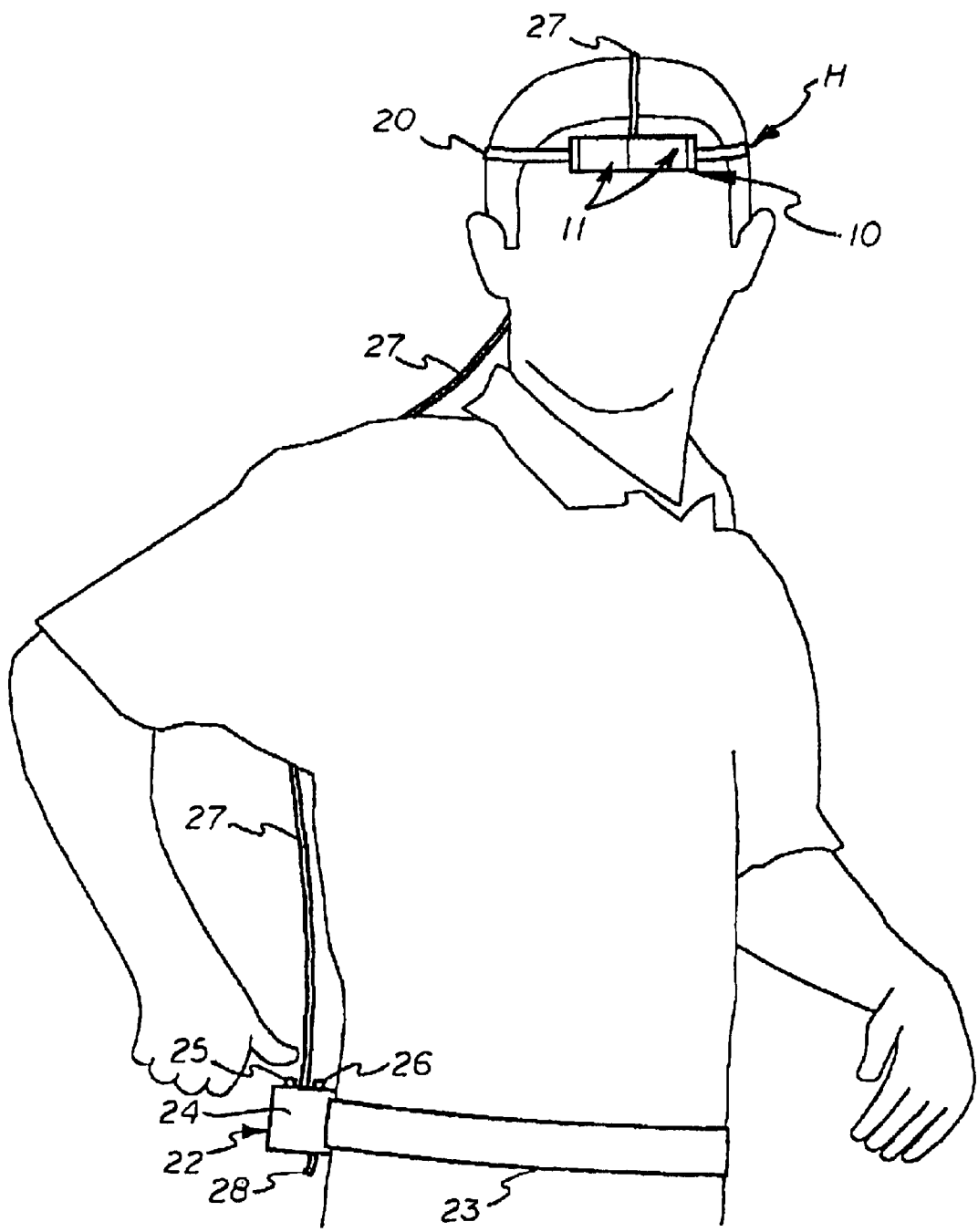
FIG. 1 is a perspective view of a person wearing a headband which incorporates a miniature solid-state thermionic heating and cooling device in accordance with the present invention.

Referring to the drawings by numerals of reference there is shown in FIG. 1, a headband H worn on the head of a person which incorporates a miniature solid-state thermionic heating and cooling device 10 in accordance with the present invention. The device 10 in the illustrated example utilizes a pair of thermionic thermal diode heating and cooling units 11 (described hereinafter) which are held in place by a securing strap 20 that is releasably fastened around the forehead of the person. It should be understood that the device may utilize one or a plurality of thermionic thermal diode heating and cooling units 11, and may also be worn on other parts of the body, such as on the person's arm or leg.

An air pump and power supply unit 22 is secured to the person's waist by a belt strap 23. The air pump and power supply unit 22 includes a small enclosure or case 24 that contains a miniature air vacuum pump and a DC battery electrically connected to the air pump motor. A commercially available air pump suitable for use is a thumb-sized model 3003, 3004 or 7006 miniature DC vacuum pump manufactured by Thomas Industries Inc. of Sheboygan, Wis. An on/off switch 25 mounted on the exterior of the case 24 is connected between the battery and the pump motor to selectively supply power to the air pump motor. A polarity reversing switch 26 mounted on the exterior of the case 24 is connected between the battery and a thermal diode module (described hereinafter) in the thermionic heating and cooling unit 11 to selectively reverse the polarity of the electrical power supplied to the thermal diode for cooling or heating. The pump, battery, and appurtenant electrical wiring and switching circuitry, which is contained within the case 24, is conventional in the art and therefore not shown in detail.

An elongate flexible air hose or tubular conduit 27 having one end connected to the intake port of the air pump inside the case 24 extends through the wall of the case and its opposed end is connected to the thermionic heating and cooling unit 11. A flexible exhaust hose or tubular conduit 28 having one end connected to the exhaust port of the air pump inside the case 24 extends through the wall of the case.

Figure 2:
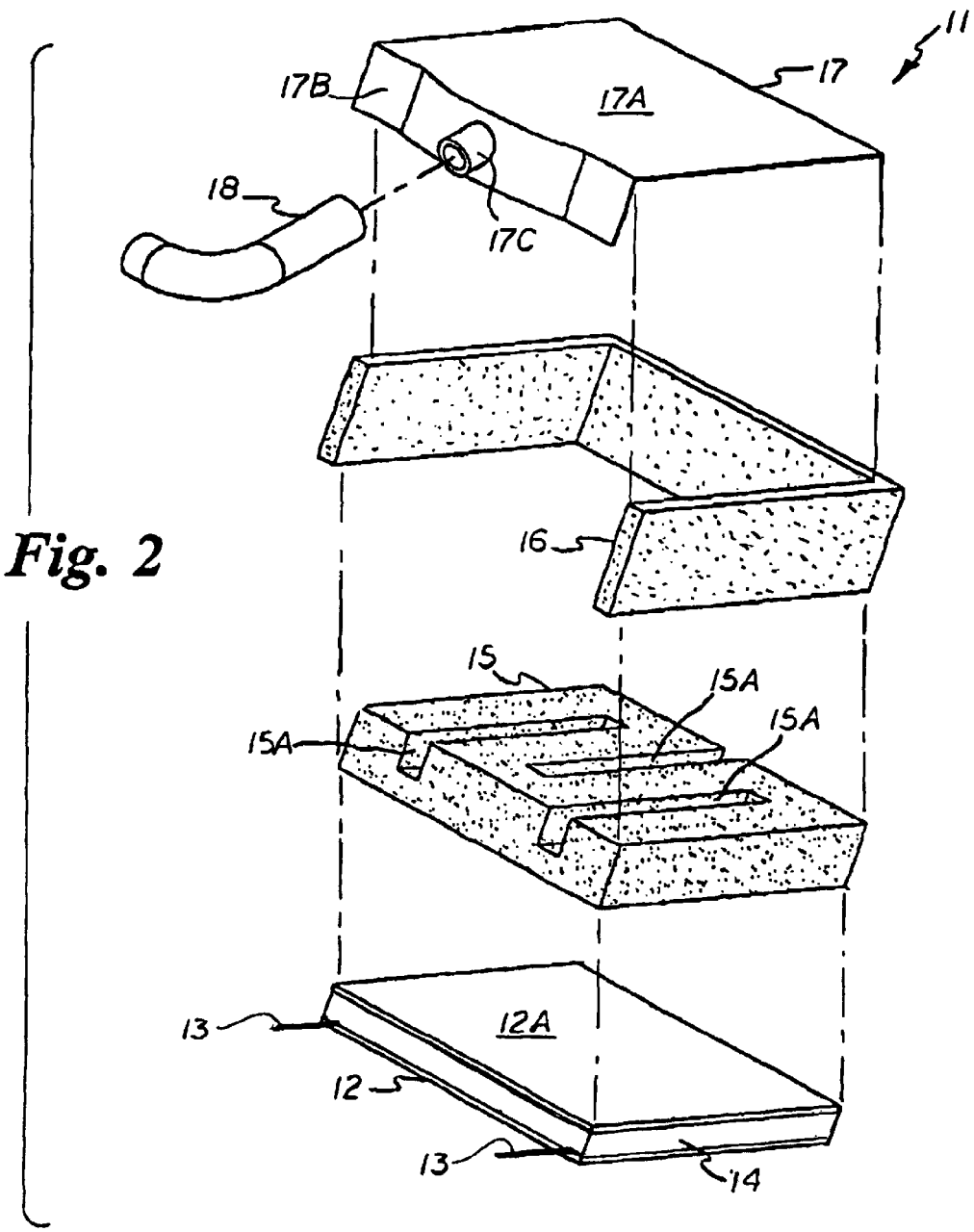
FIG. 2 is an exploded isometric view of a thermionic heating and cooling unit of the device.
Figure 3:
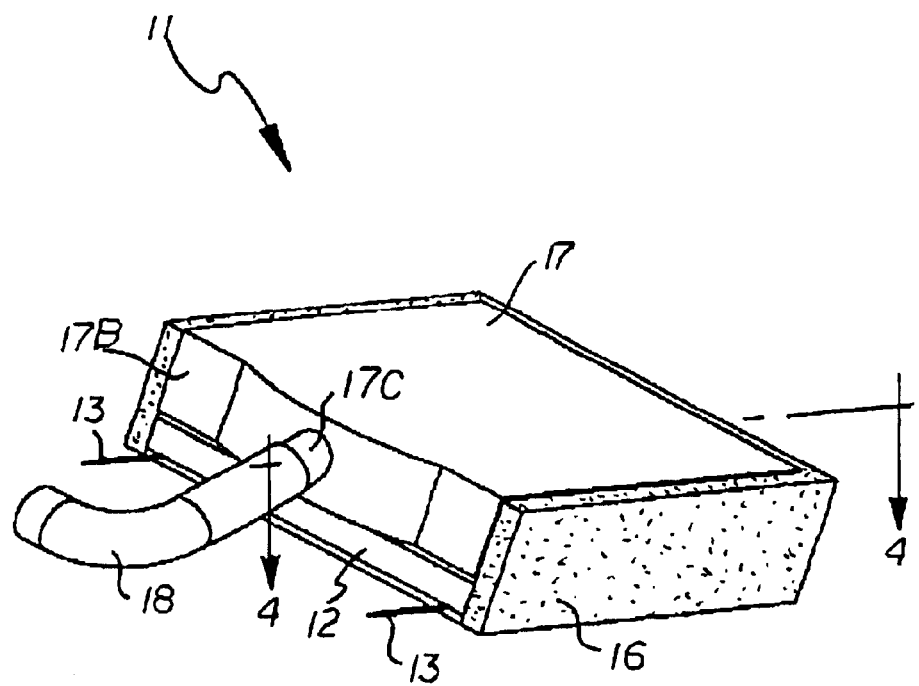
FIG. 3 is an isometric view of the thermionic heating and cooling unit in the assembled condition.
Figure 4:
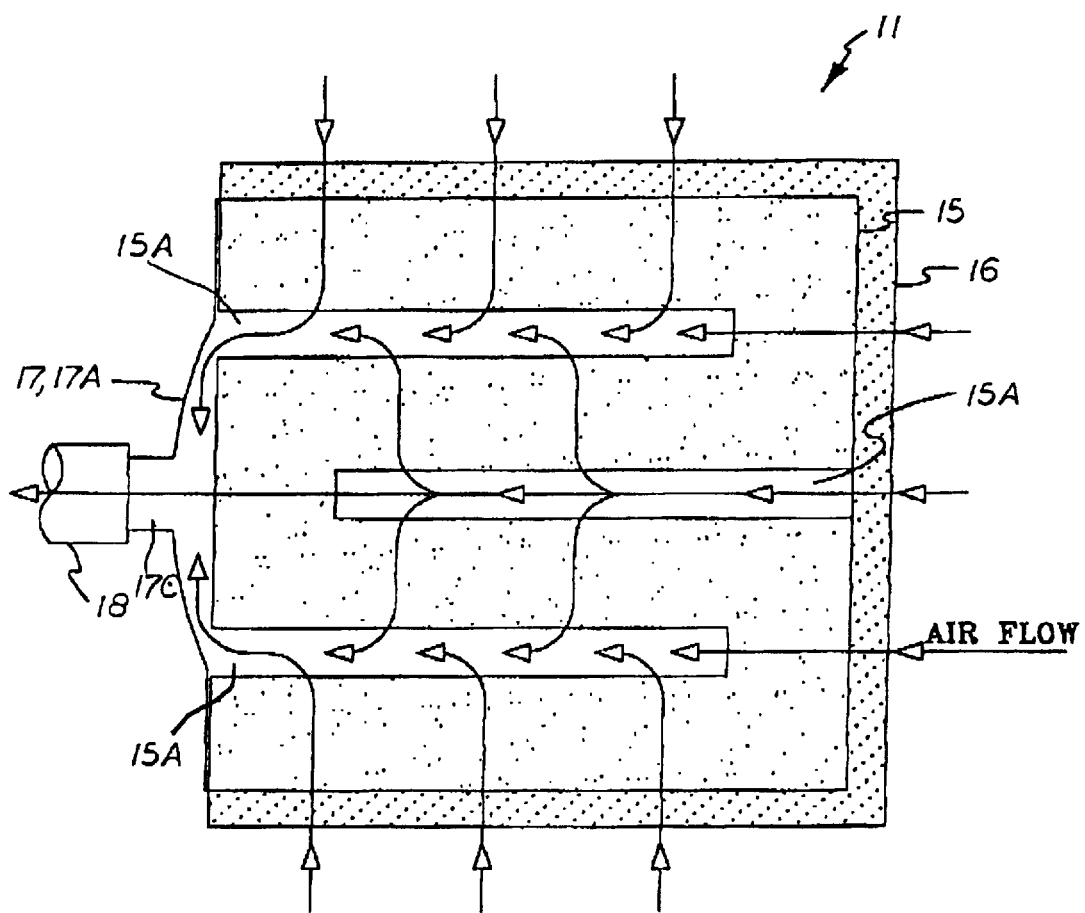
FIG. 4 is a transverse cross section through the thermionic heating and cooling unit, taken along line 4—4 of FIG. 3.

Referring now to FIGS. 2, 3 and 4, the thermionic heating and cooling unit 11 will be described in greater detail. FIG. 2 is an exploded isometric view of the solid-state thermionic heating and cooling unit 11. FIG. 3 shows the solid-state thermionic beating and cooling unit 11 in the assembled condition. The solid-state thermionic heating and cooling unit 11 includes at least one thermal diode module 12 having a pair of electrical conductors 13 attached, a carbon foam heat sink 15, a generally rectangular U-shaped air filter 16 formed of polyurethane foam having three sides sized and shaped to surround three sides of the carbon foam heat sink 15 and thermal diode module 12, and an air duct shroud 17. The air duct shroud 17 has a flat top panel 17A which covers the open top end of the air filter 16 and a depending side panel 17B which covers the remaining open side of the air filter 16 and the carbon foam heat sink 15. A nipple 17C secured on the side panel 17B has an interior in communication with the interior of the shroud 17 and an exterior configured to receive a small diameter air hose or tubular conduit 18.

The thermal diode module 12 of the present invention utilizes one or more commercially available thermal diode, vacuum diode heat pump, or tunneling diode elements which are known to those skilled in the art and therefore is represented somewhat schematically as a single rectangular module. It should be understood that the thermal diode module 12 may be disk-shaped or made up of a plurality of the small thermal diodes secured together in a single module. The construction and operation of vacuum diode heat pumps and thermal diodes of the type suitable for use in the present invention, are disclosed in U.S. Pat. Nos. 5,722,242, 6,396,191, 6,417,060 and 6,285,769, which are hereby incorporated by reference to the same extent as if fully set forth herein. The thermal diodes or vacuum diode heat pumps are small solid-state semiconductor devices capable of alternating between heating and cooling of a particular element and operate in the manner of a vacuum diode wherein the electrons move across a gap. With the addition of a voltage bias that encourages the electrons to move in a given direction, the heat is transferred from one side (cathode or emitter) to the other (anode or collector) across the gap between the two materials, and the gap prevents the heat from flowing back. The thermal diodes or vacuum diode heat pumps may have a gap that contains a suitable gas or a vacuum. The thermal diode member 12 may also utilize tunneling diodes wherein one surface of the diode element is surface is spaced apart from the other by a thin semiconductor layer and the application of a voltage difference between the surfaces causes-electrons to tunnel through the layer in one direction and transfer heat from one surface to the other and the layer prevents the heat from returning. Thermionic vacuum diode heat pump, thermal diode devices, and tunneling diodes offer much higher efficiency, higher output cooling in a much smaller package, and require less power to operate, than is possible with thermoelectric (Peltier) devices.

The hot and cold faces of the thermal diodes and/or the thermal diode module 12 may be "pre-tinned" with InSn solder which allows it to be soldered to the heat sink 15 and a metallic thermal transfer band (described hereinafter). It should be understood that the thermal diode module 12 may alternatively be coupled to the heat sink 15 and metallic thermal transfer band by other suitable means.

The carbon foam heat sink 15 is secured to one side or plate of the thermionic thermal diode module 12 in thermal exchange relation by soldering or suitable thermal coupling means such as thermal epoxy, bonding, or mechanical fasteners. The size of the carbon foam heat sink 15 is approximately 25 mm×25 mm×5 mm thick or approximately 1"×1"×3/16" thick, but may vary depending upon the number and type of thermionic diode heat pump elements useed. A plurality of air channels 15A are formed in the outer surface of the heat sink 15 and, preferably, are closed at one end.

The preferred carbon foam heat sink material utilized in the present invention is a relatively new material known as "PocoFoam"® marketed by Poco Graphite, Inc., of 1601 South Street, Decatur, Tex. 76234, which is produced by a patented foaming process disclosed in U.S. Pat. Nos. 6,033,506 and 6,037,032 issued to James W. Klett et al, and which are hereby incorporated by reference to the same extent as if fully set forth herein.

The "PocoFoam"® material is a lightweight, porous graphite foam with exceptionally high thermal conductivity and very efficient thermal energy transfer characteristics. It is produced by a proprietary foaming process that creates a structure of highly graphitic aligned ligaments within the foam's cell walls. These ligaments are the key to the material's high thermal conductivity. They perform like high performance graphite fibers, wicking heat away from its source. The carbon foam material is 3 to 9 times more thermally conductive than typical lightweight carbon foams and has thermal conductivity up to 10 limes higher than metallic foam materials, such as aluminum foam. The structure of the material has: an average pore diameter of 350 microns (0.0138 inches); a specific surface area greater than 4 $m^2/g$ (19500 $ft^2/lb$); an open porosity greater than 96%; a total porosity of 73–82%; and a density of 0.2–0.6 g/cc (12–37 $lb/ft^3$). With an active surface area of more than 4 $m^2$/g, its heat transfer efficiency is significantly greater than aluminum or copper foam material and finned heat sinks.

Figure 5:
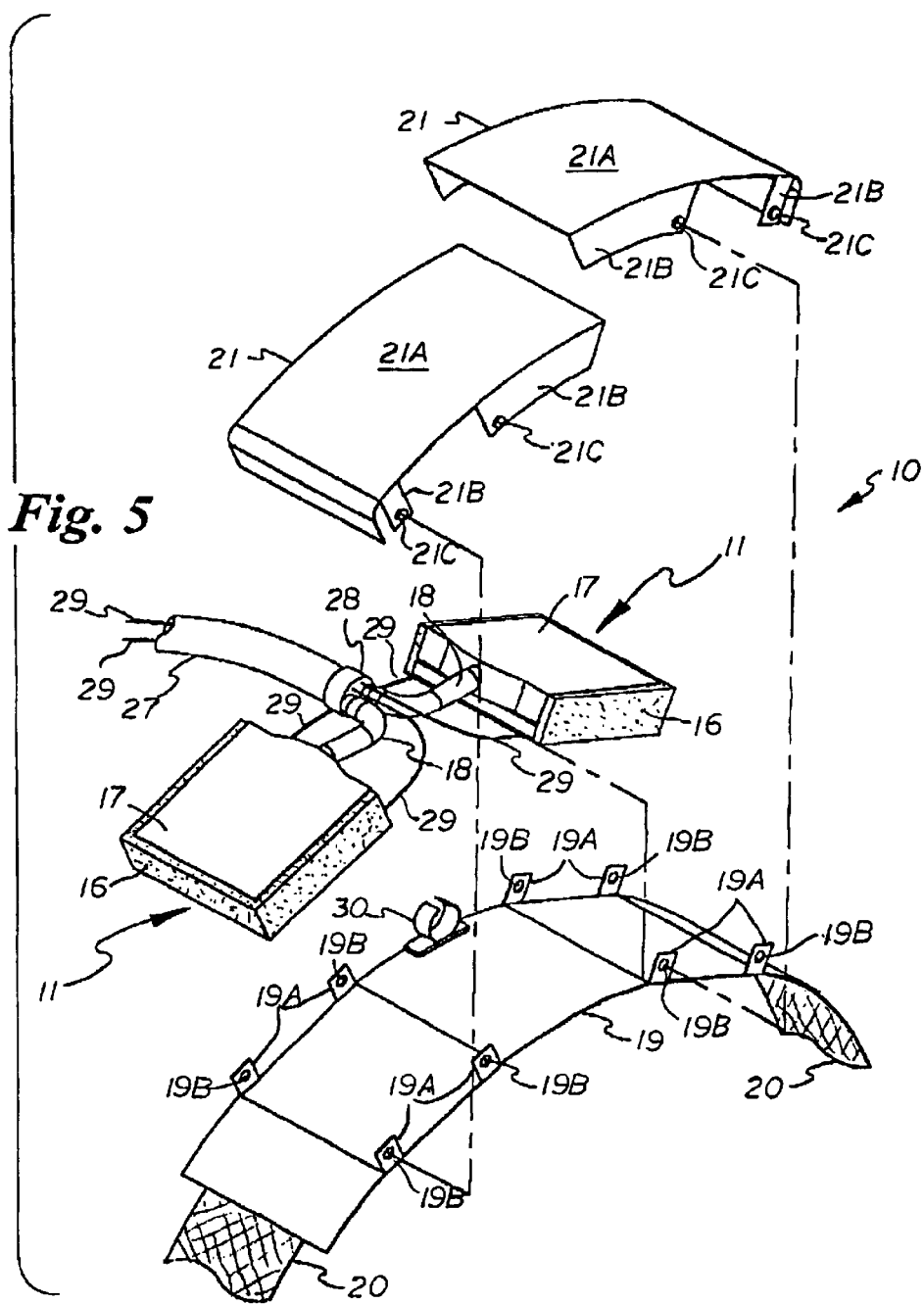
FIG. 5 is an exploded isometric view of the headband assembly which incorporates a pair of thermionic heating and cooling units.
Figure 6:
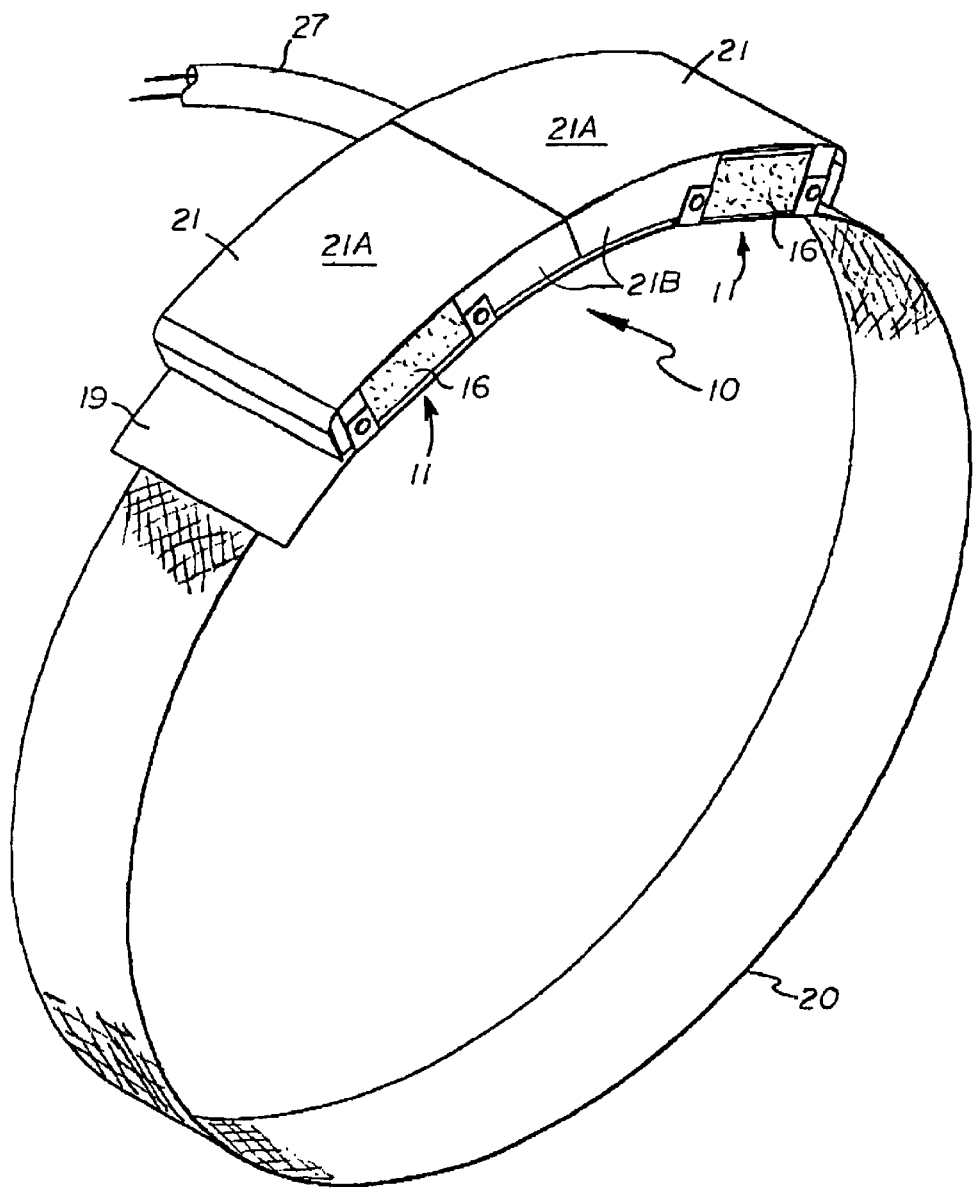
FIG. 6 is an isometric view of the headband assembly in the assembled condition.

Referring now to FIGS. 1, 5 and 6, in the headband example, a pair of the thermionic heating and cooling units 11 described above are utilized. In this example, the flexible air conduit 27 which is connected to the intake port of the air pump inside the air pump and power supply case 24 (FIG. 1) has a hose splitter coupling 28 connected at its opposed end. Each of the outer ends of the coupling 28 is joined to the nipple 17C of the shroud 17 of a respective heating and cooling unit 11 by the short air conduit 18, and thus the interior of the air conduit 27 is in fluid communication with the interior of both heating and cooling units 11. Two pairs of insulated electrical leads 29 extend through interior of the flexible air conduit 27 and pass through the hose splitter coupling 28. One end of each wire of each pair of leads 29 is connected to the positive terminal and the other wire is connected to the negative terminal, respectively, of the battery inside the air pump and power supply case 24 through the polarity reversing switch 26. The opposed end of each wire of each pair of leads 29 is connected to a respective conductor 13 of the thermionic thermal diode modules 12.

A flexible metallic thermal transfer band 19 formed of suitable thermally conductive material such as copper is connected at each end to the securing strap 20 that is to be releasably fastened around the forehead of the user. In this example, the size of the metallic thermal transfer band 19 is approximately 30 mm wide×100 mm long and 0.6 mm thick or approximately 1-3/16" wide×4" long and 1/32" thick. The thermionic heating and cooling units 11 are secured to the outer surface of the thermal transfer band 19 in laterally opposed relation by soldering or other suitable thermal coupling means such as thermal epoxy, bonding or mechanical fasteners. A hose clamp 30 may also be secured to the thermal transfer band 19 for receiving and gripping the air conduit 27.

A plurality of longitudinally spaced upstanding tabs 19A are formed along the longitudinal sides of the thermal transfer band 19 and each has an aperture 19B therethrough. A pair of protective covers 21 each have a top panel 21A, which covers the top end of a respective thermionic heating and cooling unit 11, and pair of side portions 21B depending from the longitudinal sides of the top panel which are provided with outwardly extending protuberances 21C. The covers 21 are installed over the thermionic heating and cooling units 11 by pressing them down such that the protuberances 21C snap fit into the apertures 19B of the upstanding tabs 19A of the thermal transfer band 19. The opposed facing ends covers 21 are sized and shaped to overlap and slide over one another so that the thermal transfer band 19, may flex to accommodate the shape of the forehead. The side portions 21B are sized and spaced apart to expose a major portion of the air filter 16. The metallic thermal transfer strip 19 serves as a base from which thermal energy is absorbed from an area relatively larger than the thermionic heating and cooling units 11. Using two of the thermionic heating and cooling units 11 distributes the thermal exchange across a wider area of the forehead of the operator thereby maximizing comfort.

Operation

Referring to FIG. 1, the headband assembly H, is secured to a person's forehead by use the securing strap 20 and the power supply and air pump unit 22 is secured to the waist of the person by the belt strap 23. The polarity-reversing switch 26 is turned to the "cool" position if cooling is desired, or to the "heat" position if heating is desired. The power on/off switch 25 is turned to the "on" position to activate the air pump and energize the thermal diode modules 12.

When energized, the thermal diode modules 12, absorb heat from the metallic thermal transfer band 19 and the voltage bias causes the electrons to move in a given direction and the heat is transferred from one side (cathode or emitter) to the other (anode or collector) across the gap between the two faces of the thermal diodes or vacuum diode heat pumps, and the gap prevents the heat from flowing back. The gap of the thermal diode modules 12, may contain a suitable gas or a vacuum. The thermal diode member 12 may also utilize tunneling diodes wherein one surface of the diode element is surface is spaced apart from the other by a thin semiconductor layer and the application of a voltage difference between the surfaces causes electrons to tunnel through the layer in one direction and transfer heat from one surface to the other and the layer prevents the heat from returning. The trapped thermal energy is transferred to the carbon foam heat sink 15. The sealant 14 on the thermal diode modules 12 protects the internal components of the module from condensate of the ambient air that may be produced by low operating temperatures.

As indicated by the arrows in FIG. 4, ambient air is drawn through the air filter 16, before entering the microscopic porous pathways of the carbon foam heat sink 15, wherein thermal energy is absorbed and removed by the passing air. The air filter 16 prevents minute airborne particles from entering and clogging the microscopic pathways of the carbon foam heat sink 15. The air channels 15A in the carbon foam heat sink 15, are preferably closed at one end to direct and facilitate even distribution of the incoming air throughout the entire cellular structure of the porous carbon foam heat sink material so that an even thermal transfer will occur throughout the entire carbon foam heat sink, thereby maximizing thermal transfer efficiency. The air duct shroud 17 directs the drawn air through the course described above and eventually returns warm air through the air conduits 18 and 27 where it is discharged through the heat exhaust conduit 28.

Unlike thermoelectric (Peltier) devices which carry heat in one direction through the material itself and lose most of that heat through conduction, the gap or semiconductor layer of the thermionic thermal diode devices, vacuum diode heat pump devices, or tunneling diode devices of the present invention prevents heat from returning and provide. much higher efficiency, higher output cooling in a much smaller package, and require less power to operate than is possible with thermoelectric (Peltier) devices.

Unlike conventional finned heat sinks, air does not pass over and around the outer surfaces of fins, but instead is drawn through the open pore cellular structure of the carbon foam material. The highly graphitic aligned ligaments within the foam's cell walls perform like high performance graphite fibers, wicking the heat away from its source and provide high thermal conductivity. More than 96% of the porosity is interconnected, or open, porosity, which provides a very high internal surface area. This, in turn, produces significantly more efficient heat transfer to the air passing through that porosity.

The air, after passing through the carbon foam heat sink 15, is returned to the air pump and discharged through the heat exhaust conduit 28. The heat exhaust conduit can be of any length, allowing the operator to be cooled while wearing hazardous material suits, fire fighting equipment, military equipment, costumes, or plain street clothes. The headband assembly H has a thin profile, being approximately 8 mm (5/16") or less. This profile allows the headband assembly to be worn and concealed beneath hardhats, safety helmets, military helmets, uniform hats, ball caps, headbands or no head cover at all.

While this invention has been described fully and completely with special emphasis upon a preferred embodiment, it should be understood that within the scope of the appended claims the invention may be practiced otherwise than as specifically described herein.

What is claimed is:

1. A miniaturized solid-state thermionic heating and cooling module, comprising in combination:

at least one thermionic diode member selected from the group consisting of vacuum diode heat pumps, thermal diodes, tunneling diodes, and tunneling vacuum diodes;

said thermionic diode member having a first surface spaced apart from a second surface wherein the application of a voltage difference between said surfaces creates a cold surface and hot surface opposite each other and causes electrons to flow substantially in one direction between said spaced apart surfaces and transfer heat from said first surface to said second surface;

coupling means connected with said thermionic diode member for coupling a source of polarized electrical energy thereto to energize said thermionic diode member;

a porous carbon foam heat sink member secured on said thermionic diode member second surface in thermal exchange relation, said carbon foam heat sink member formed of a thermally conductive open cell foam medium through which air can pass, and having at least one channel formed therein configured to direct incoming air into and facilitate even distribution thereof through the cellular structure of the porous carbon foam medium;

a shroud partially enclosing said porous carbon foam heat sink member; and a conduit having a first end connected in fluid communication with said shroud and a second end adapted for connection to an air pump for drawing ambient air through said thermally conductive open cell foam medium.

2. The module according to claim 1, wherein said thermionic diode member first surface is spaced apart from a second surface by a gap wherein the application of a voltage difference between said surfaces causes electrons to flow across said gap in one direction and transfer heat from said first surface to said second surface, and said gap prevents the heat from returning to said first surface.

3. The module according to claim 1, wherein said thermionic diode member first surface is spaced apart from a second surface by a vacuum wherein the application of a voltage difference between said surfaces causes electrons to flow through said vacuum in one direction and transfer heat from said first surface to said second surface, and said vacuum prevents the heat from returning to said first surface.

4. The module according to claim 1, wherein said thermionic diode member first surface is spaced apart from a second surface by a thin semiconductor layer wherein the application of a voltage difference between said surfaces causes electrons to tunnel through said layer in one direction and transfer heat from said first surface to said second surface, and said layer prevents the heat from returning to said first surface.

5. The module according to claim 1, wherein said open cell foam medium is a lightweight, porous graphite foam with an average pore diameter of approximately 350 microns (approximately 0.0138 inches).

6. The module according to claim 1, wherein said open cell foam medium has an effective heat exchanging surface area greater than about 4 m²/g (about 19500 ft²/lb).

7. The module according to claim 1, further comprising:
an air filter partially surrounding said porous carbon foam heat sink member and said thermionic diode member and adjoined with said shroud; wherein
said shroud and said air filter cooperatively substantially surround said porous carbon foam heat sink member and filtered ambient air is drawn through said thermally conductive open cell foam medium.

8. A personal solid state thermionic heating and cooling device for heating or cooling a portion of a user's body, comprising:
a flexible thermal transfer band formed of thermally conductive material having a user-facing surface adapted to engage a portion of the user's body, an outer-facing surface, and means for releasably securing said thermal transfer band on said portion of the user's body;
at least one thermionic diode member having a first surface secured on said thermal transfer band outer-facing surface in thermal transfer relation and a second surface spaced therefrom wherein the application of a voltage difference between said surfaces creates a cold surface and hot surface opposite each other and causes electrons to flow substantially in one direction between said spaced apart surfaces and transfer heat from said first surface to said second surface;
a porous carbon foam heat sink member secured on said thermionic member second surface in thermal exchange relation, said carbon foam heat sink member formed of a thermally conductive open cell foam medium through which air can pass;
a shroud partially enclosing said porous carbon foam heat sink member;
a small enclosure with means for releasably securing said enclosure on another portion of the user's body remote from said thermal transfer band;
a motorized air pump contained in said enclosure having an inlet and an outlet;
a battery contained within said enclosure electrically connected with said motorized air pump through switch means on said enclosure for selectively energizing said air pump;
a flexible tubular conduit having a first end connected to said air pump inlet and a second end connected in fluid communication with said shroud for drawing ambient air through said thermally conductive open cell foam medium; and
electrical leads having first ends electrically connected with said battery and second ends connected with said thermionic diode member through a polarity reversing switch on said enclosure for supplying selective polarized electrical energy thereto to energize said thermionic diode member.

9. The device according to claim 8, wherein
said thermionic diode member is selected from the group consisting of vacuum diode heat pumps, thermal diodes, tunneling diodes, and tunneling vacuum diodes.

10. The device according to claim 8, wherein
said thermionic diode member first surface is spaced apart from a second surface by a gap wherein the application of a voltage difference between said surfaces causes electrons to flow across said gap in one direction and transfer heat from said first surface to said second surface, and said gap prevents the heat from returning to said first surface.

11. The device according to claim 8, wherein
said thermionic diode member first surface is spaced apart from a second surface by a vacuum wherein the application of a voltage difference between said surfaces causes electrons to flow through said vacuum in one direction and transfer heat from said first surface to said second surface, and said vacuum prevents the heat from returning to said first surface.

12. The device according to claim 8, wherein
said thermionic diode member first surface is spaced apart from a second surface by a thin conductor layer wherein the application of a voltage difference between said surfaces causes electrons to tunnel through said layer in one direction and transfer heat from said first surface to said second surface, and said layer prevents the heat from returning to said first surface.

13. The device according to claim 8, wherein
said open cell foam medium is a lightweight, porous graphite foam with an average pore diameter of approximately 350 microns (approximately 0.0138 inches).

14. The device according to claim 8, wherein
said open cell foam medium has an effective heat exchanging surface area greater than about 4 m² /g (about 19500 ft² / lb).

15. The device according to claim 8, wherein
said porous carbon foam heat sink member has at least one channel formed therein configured to direct incoming air into and facilitate even distribution thereof through the cellular structure of the porous carbon foam medium.

16. The device according to claim 8, further comprising:
an air filter partially surrounding said porous carbon foam heat sink member and said thermionic member and adjoined with said shroud; wherein
said shroud and said air filter cooperatively substantially surround said porous carbon foam heat sink member and filtered ambient air is drawn through said thermally conductive open cell foam medium.

17. The device according to claim 8, wherein
said electrical leads extend through the interior of said flexible tubular conduit, with said first and seconds ends being disposed exterior thereof.

18. The device according to claim 8, wherein
there are a plurality of said thermionic diode members each having its said first surface secured on said thermal transfer band outer-facing surface in thermal transfer relation with said porous carbon foam heat sink member secured on their said second surface in thermal exchange relation, and said shroud partially enclosing each said porous carbon foam heat sink member; and
said flexible tubular conduit has a first end connected to said air pump inlet and a second end connected by individual tubular conduits in fluid communication with each respective said shroud for drawing ambient air through said thermally conductive open cell foam medium.

19. The device according to claim 18, further comprising:
an air filter partially surrounding each said porous carbon foam heat sink member and said thermionic diode members and adjoined with a respective said shroud; wherein said shroud and said air filter cooperatively substantially surround said porous carbon foam heat sink and filtered ambient air is drawn through said thermally conductive open cell foam medium.

20. The device according to claim 19, further comprising:
a plurality of protective covers each sized and shaped to cover a portion of a respective said porous carbon foam heat sink member, thermionic diode member, and shroud, and having side portions sized and spaced apart to expose a major portion of said air filter; and
portions of adjacent ones of said covers sized and shaped to overlap and slide relative to one another to allow said thermal transfer band to flex to accommodate the shape of the portion of the user's body which it is engaged.

21. A miniaturized solid-state thermionic heating and cooling module, comprising in combination:
at least one thermionic diode member having a first surface spaced apart from a second surface wherein the application of a voltage difference between said surfaces creates a cold surface and hot surface opposite each other and causes electrons to flow substantially in one direction between said spaced apart surfaces and transfer heat from said first surface to said second surface;
coupling means connected with said thermionic diode member for coupling a source of polarized electrical energy thereto to energize said thermionic diode member; and
a porous carbon foam heat sink member secured on said thermionic diode member second surface in thermal exchange relation, said carbon foam heat sink member formed of a thermally conductive open cell foam medium through which air can pass, and having at least one channel formed therein closed at one end to direct incoming air into and facilitate even distribution thereof throughout the cellular structure of the porous carbon foam medium.

* * * * *